United States Patent
Sanghera et al.

(10) Patent No.: US 8,712,523 B2
(45) Date of Patent: Apr. 29, 2014

(54) IMPLANTABLE DEFIBRILLATOR SYSTEMS AND METHODS WITH MITIGATIONS FOR SATURATION AVOIDANCE AND ACCOMMODATION

(75) Inventors: Rick Sanghera, San Clemente, CA (US); Venugopal Allavatam, Oceanside, CA (US); Surekha Palreddy, Maplewood, MN (US); Jay A. Warren, San Juan Capistrano, CA (US)

(73) Assignee: Cameron Health Inc., San Clemente, CA (US)

( * ) Notice: Subject to any disclaimer, the term of this patent is extended or adjusted under 35 U.S.C. 154(b) by 1173 days.

(21) Appl. No.: 12/636,575

(22) Filed: Dec. 11, 2009

(65) Prior Publication Data

US 2010/0152799 A1    Jun. 17, 2010

Related U.S. Application Data

(60) Provisional application No. 61/122,327, filed on Dec. 12, 2008.

(51) Int. Cl.
*A61N 1/37* (2006.01)

(52) U.S. Cl.
CPC ............ *A61N 1/3704* (2013.01); *A61N 1/3702* (2013.01)
USPC .......................................................... 607/27

(58) Field of Classification Search
CPC ..... A61N 1/37; A61N 1/3702; A61N 1/3704; A61N 1/371
USPC .......................................... 607/27–28, 4–5, 9
See application file for complete search history.

(56) References Cited

U.S. PATENT DOCUMENTS

| | | |
|---|---|---|
| 4,184,493 A | 1/1980 | Langer et al. |
| 4,300,567 A | 11/1981 | Kolenik et al. |
| 4,407,288 A | 10/1983 | Langer et al. |
| 4,450,527 A | 5/1984 | Sramek |
| 4,457,315 A | 7/1984 | Bennish |
| 4,567,900 A | 2/1986 | Moore |
| 4,595,009 A | 6/1986 | Leinders |
| 4,603,705 A | 8/1986 | Speicher et al. |
| 4,679,144 A | 7/1987 | Cox et al. |

(Continued)

FOREIGN PATENT DOCUMENTS

EP        0554208 A2    8/1993

OTHER PUBLICATIONS

Gunderson et al., "An Algorithm to Predict Implantable Cardioverter-Defibrillator Lead Failure," JACC, Nov. 2004, vol. 44, No. 9, pp. 1898-1902.

(Continued)

*Primary Examiner* — Carl H Layno
*Assistant Examiner* — Jessica Anthony
(74) *Attorney, Agent, or Firm* — Schwegman, Lundberg & Woessner, P.A.

(57) ABSTRACT

Methods and implantable devices that address response to, or avoidance of, likely non-cardiac voltages including after potentials from external or internal stimulus. Also, methods of operation in implantable medical devices, the methods configured for identifying saturation of input circuitry and mitigating the effects of such saturation. Also, implantable cardiac stimulus or monitoring devices that include methods for identifying saturated conditions and mitigating the effects of such saturation.

18 Claims, 10 Drawing Sheets

(56) References Cited

U.S. PATENT DOCUMENTS

| | | |
|---|---|---|
| 4,693,253 A | 9/1987 | Adams |
| 4,750,494 A | 6/1988 | King |
| 4,779,617 A | 10/1988 | Whigham |
| 4,944,300 A | 7/1990 | Saksena |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,271,411 A | 12/1993 | Ripley et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,342,402 A | 8/1994 | Olson et al. |
| 5,342,407 A | 8/1994 | Dahl et al. |
| 5,351,696 A | 10/1994 | Riff et al. |
| 5,376,104 A | 12/1994 | Sakai et al. |
| 5,423,326 A | 6/1995 | Wang et al. |
| 5,486,199 A | 1/1996 | Kim et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,607,455 A | 3/1997 | Armstrong |
| 5,618,287 A | 4/1997 | Fogarty et al. |
| 5,658,317 A | 8/1997 | Haefner et al. |
| 5,709,215 A | 1/1998 | Perttu et al. |
| 5,755,742 A | 5/1998 | Schuelke et al. |
| 5,776,168 A | 7/1998 | Gunderson |
| 5,817,134 A | 10/1998 | Greenhut et al. |
| 5,827,197 A | 10/1998 | Bocek et al. |
| 5,857,977 A | 1/1999 | Caswell et al. |
| 5,991,657 A | 11/1999 | Kim |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Grey |
| 6,148,230 A | 11/2000 | Kenknight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,117,035 B2 | 10/2006 | Wagner et al. |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson |
| 7,302,294 B2 | 11/2007 | Kamath et al. |
| 7,330,757 B2 | 2/2008 | Ostroff et al. |
| 7,346,392 B2 | 3/2008 | Kenknight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,474,247 B1 | 1/2009 | Heinks et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 2004/0049120 A1 | 3/2004 | Cao et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2004/0254611 A1 | 12/2004 | Palreddy et al. |
| 2005/0107838 A1 | 5/2005 | Lovett et al. |
| 2005/0131464 A1 | 6/2005 | Heinrich et al. |

(56) References Cited

U.S. PATENT DOCUMENTS

| | | |
|---|---|---|
| 2005/0154421 A1 | 7/2005 | Ousdigian |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis et al. |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0015647 A1 | 1/2008 | Palreddy et al. |
| 2008/0045850 A1 | 2/2008 | Phillips |
| 2008/0077030 A1 | 3/2008 | Ostroff et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | Van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0269835 A1 | 10/2008 | Carlson et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2008/0300497 A1* | 12/2008 | Krause et al. ............. 600/515 |
| 2009/0036788 A1 | 2/2009 | Nabutovsky et al. |
| 2009/0043352 A1 | 2/2009 | Brooke et al. |
| 2009/0054796 A1 | 2/2009 | Marcovecchio et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0187227 A1 | 7/2009 | Palreddy et al. |
| 2009/0228057 A1 | 9/2009 | Allavatam et al. |
| 2009/0240157 A1 | 9/2009 | Liam et al. |
| 2009/0240300 A1 | 9/2009 | Liam et al. |
| 2009/0259271 A1 | 10/2009 | Allavatam et al. |
| 2010/0004713 A1 | 1/2010 | Warren et al. |
| 2010/0023084 A1 | 1/2010 | Gunderson |
| 2010/0076515 A1 | 3/2010 | Phillips |
| 2010/0094369 A1 | 4/2010 | Allavatam et al. |
| 2010/0152798 A1 | 6/2010 | Sanghera et al. |
| 2010/0331904 A1 | 12/2010 | Warren et al. |
| 2011/0098585 A1 | 4/2011 | Warren et al. |
| 2011/0098775 A1 | 4/2011 | Allavatam et al. |

OTHER PUBLICATIONS

Olson et al., "Onset and Stability for Ventricular Tachyarrhythmia Detection in an Implantable Pacer-Cardioverter Defibrillator," IEEE, (1987) pp. 167-170.

Schuder, "The Role of an Engineering Oriented Medical Research Group in Developing Improved Methods and Devices for Achieving Ventricular Defibrillation: The University of Missouri Experience," PACE, vol. 16, Jan. 1993, pp. 95-124.

Schwake et al., "Komplikationen nit Sonden bei 340 Patienten mit einem Implantierbaren Kardioverter/Defibrillator," Z Kardiol (1999)vol. 88, No. 8 pp. 559-565.

Swerdlow, et al., "Advanced ICD Troubleshooting: Part I," online article at http://www.medscape.com/viewarticle/520588_print, accessed and printed Jul. 7, 2009, indicates publication Jan. 9, 2006 (publication date not confirmed).

Throne, "A Comparison of Four New Time-Domain Techniques for Discriminating Monomorphic Ventricular Tachycardia from Sinus Rhythm Using Ventricular Waveform Morphology," IEEE Transactions on Biomedical Engineering, vol. 38, No. 6, Jun. 1991, pp. 561-570.

USPTO Office Action (May 23, 2012)—U.S. Appl. No. 12/625,050 (Phillips).

International Search Report and Written Opinion for PCT / US2009 / 067782; issued May 10, 2010.

* cited by examiner

IMPLANTABLE DEFIBRILLATOR SYSTEMS AND METHODS WITH MITIGATIONS FOR SATURATION AVOIDANCE AND ACCOMMODATION

RELATED APPLICATIONS

The present application claims the benefit of and priority to U.S. Provisional Patent Application No. 61/122,327, filed 12 Dec. 2008, titled IMPLANTABLE DEFIBRILLATOR SYSTEMS AND METHODS WITH MITIGATIONS FOR SATURATION AVOIDANCE AND ACCOMMODATION, and the disclosure of which is incorporated herein by reference. The present Application is related to U.S. patent application Ser. No. 12/636,569, now U.S. Pat. No. 8,483,841, filed Dec. 11, 2009, titled ELECTRODE SPACING IN A SUBCUTANEOUS IMPLANTABLE CARDIAC STIMULUS DEVICE, which also claims the benefit of and priority to U.S. Provisional Patent Application 61/122,327, and is also incorporated herein by reference.

FIELD

The present invention relates to the field of implantable medical devices. More particularly, the present invention relates to implantable cardiac stimulus and/or monitoring devices.

BACKGROUND

Implantable cardioverter-defibrillators are known in the art. Prior devices have included transvenous devices that include leads that reside in blood vessels and electrodes placed in or on the heart, or epicardial devices that include electrodes placed on the outside of the heart. Newer alternatives may include subcutaneous-only systems which lack leads in or on the heart. One challenge in designing any implantable system is the proper handling of signals if/when input circuitry becomes saturated due to internal or external electrical events.

SUMMARY

The present invention includes several embodiments that are directed toward device response to, or avoidance of, residual voltages following external or internal stimulus. Some illustrative examples are directed toward methods for identifying and handling input circuitry saturation. The following illustrative examples may be embodied in methods of operation, methods of implantation, and/or as implantable components and systems.

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives.

Figure 1:
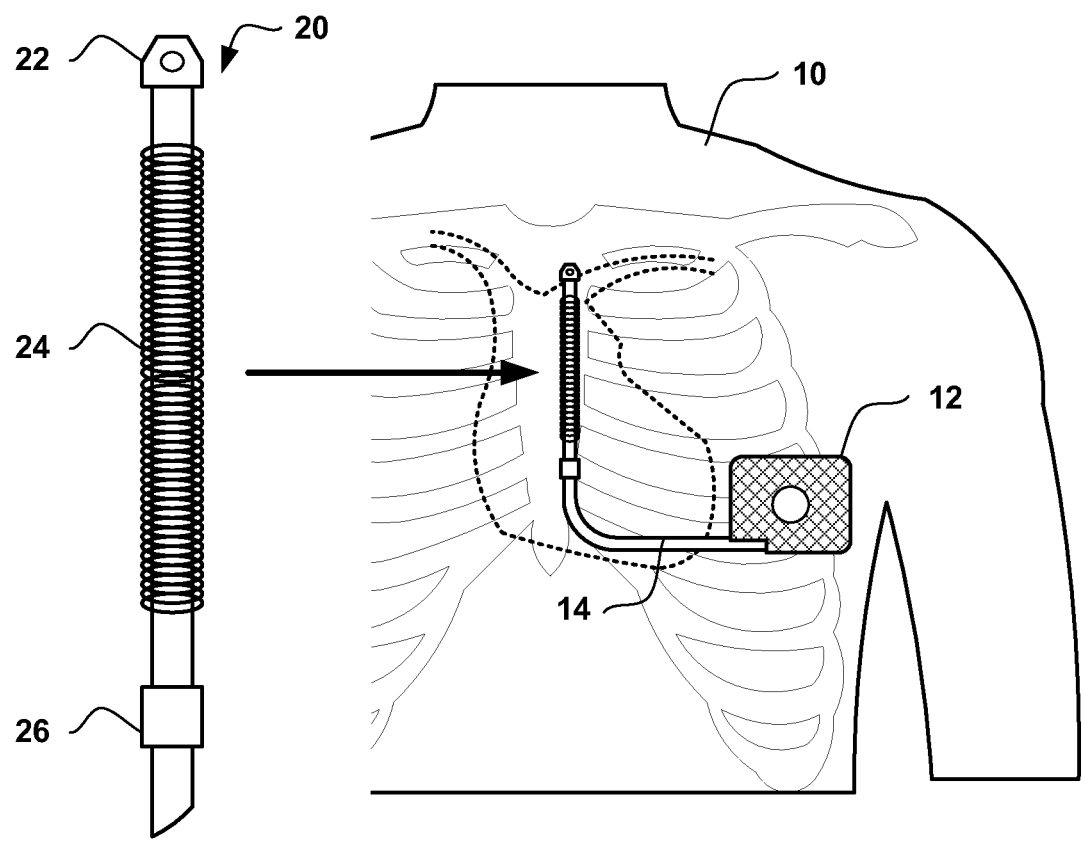
FIG. 1 is a schematic view of an illustrative subcutaneously implanted system relative to the anatomy of an implantee.

FIG. 1 illustrates features of a subcutaneously implanted cardiac stimulus system relative to the anatomy of an implantee 10. The illustrative implant is subcutaneous-only, and there is no electrode or lead assembly in or in contact with the heart or heart tissue, and no lead assembly or other component residing in the vasculature. Instead, the illustrative system includes a canister 12 attached to a lead 14, and both are disclosed subcutaneously, between the ribcage and the skin of the patient 10. The canister 12 is disposed near the axilla of the patient, at about the level of the cardiac apex and the inframammary crease. The lead 14 extends in a medial direction to approximately the xiphoid and then toward the head of the patient along the left side of the sternum, terminating near the top of the sternum. In an alternative embodiment, one or more leads may be placed in or on the heart. The canister 12 may have one or several electrodes. A lead may be omitted, with the canister having all needed electrodes thereon, if desired. Other designs may be used with the present invention including, and without limitation, transvenous systems, intravascular systems, epicardial systems, and systems having combinations of one or more of subcutaneous, transvascular, epicardial leads, active canisters, and/or multiple canister electrodes.

As shown in the detail view at 20, the lead 14 includes a distal sensing electrode 22, a therapy delivery coil 24 and a proximal sensing electrode 26. ("Distal" and "Proximal" refer to position along the lead 14, with the distal electrode 22 being farthest from the lead 14 connection to the canister 12). The distal sensing electrode 22 may, as shown, include a suture hole useful for securing the distal sensing electrode 22 to subcutaneous tissue upon implantation. If desired, the therapy delivery coil 24 may be used as a sensing electrode, and one or more of the sensing electrodes 22, 26 may also be used as therapy delivery electrodes. Different arrangements of the electrodes (distal tip as coil, multiple sense electrodes distal of the coil, and/or additional proximal electrodes) may be used, and the electrode designs shown are merely illustrative. The canister 12 may also include a suture feature (such as a suture hole in the header) for securing to subcutaneous tissue. In some examples, a suture sleeve is provided on the lead 14, for example, near the xiphoid, to provide an additional point of fixation or as a substitute for the suture hole on the distal electrode 22. Multiple leads may be provided, if desired.

The lead 14 may include multiple separate conductors for the several electrodes 22, 24, 26 and the lead 14 may be described as a lead electrode assembly, without limiting lead 14 to any particular internal structure or manner of construction. This example is merely illustrative. Additional implantation locations are shown, for example, in commonly owned U.S. patent application Ser. No. 11/006,291, published as US 2006-0122676 A1, now U.S. Pat. No. 7,655,014, and titled APPARATUS AND METHOD FOR SUBCUTANEOUS ELECTRODE INSERTION, and/or U.S. Pat. Nos. 6,647, 292, 6,721,597 and 7,149,575; any of the implantation locations shown in these patents and applications may be used as well. In one example, a system having the three-electrode lead 14 and active canister 12 as shown in FIG. 1 is implanted with the active canister 12 disposed approximately anterior of the left axilla with the lead 14 extending past the axilla to a location over the posterior region of the ribs of the patient, with the distal end of the lead to the left of the spine of the patient, creating an anterior-posterior vector between the active canister and the coil electrode 24. The '292 patent includes certain unitary embodiments, which may also be used, as desired. Epicardial or transvenous systems are shown, for example, in U.S. Pat. Nos. 4,603,705, 4,693,253, 4,944,300, 5,105,810, 4,567,900 and/or 5,618,287. Other locations, systems and combinations may be used.

The system may include any suitable components for detection and control (such as an input ECG amplifier, filtering circuitry, analog-to-digital conversion circuitry, memory, a microcontroller, etc.), telemetry (such as an antenna, amplifier, mixer, transceiver, etc.), power supply (any suitable battery technology may be used) and output circuitry (such as switches, high-power capacitors, and charging circuitry). Any suitable materials may be used for the lead 14 and canister 12. An illustrative example includes a titanium canister 12 having a titanium nitride coating, a polyurethane body for the lead 14 with a silicone sheath thereon, and MP35N conductors in the lead 14 and electrodes 22, 24, 26. Various other materials are known in the art and may be substituted for any of these items. Illustrative additional or alternative design details include iridium oxide or porous carbon coatings, platinum or silver electrodes, conductors and/or canister materials, and other materials for the body of lead 14. Drawn filled tubes are known for the conductors as well. Other structures and components may be used; those noted here are for illustrative purposes only and the invention is not limited to these particular examples.

Figure 2:
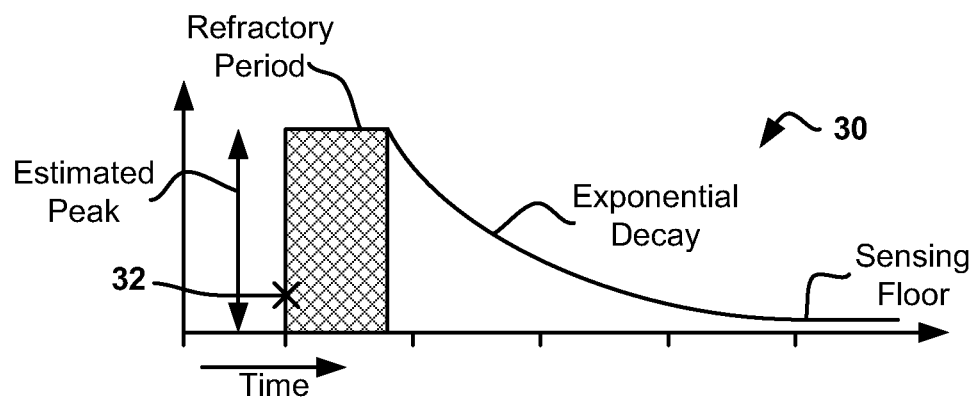
FIGS. 2-3 are graphic representations of detection profiles for use in detecting cardiac events with an illustrative implantable system.
Figure 3:
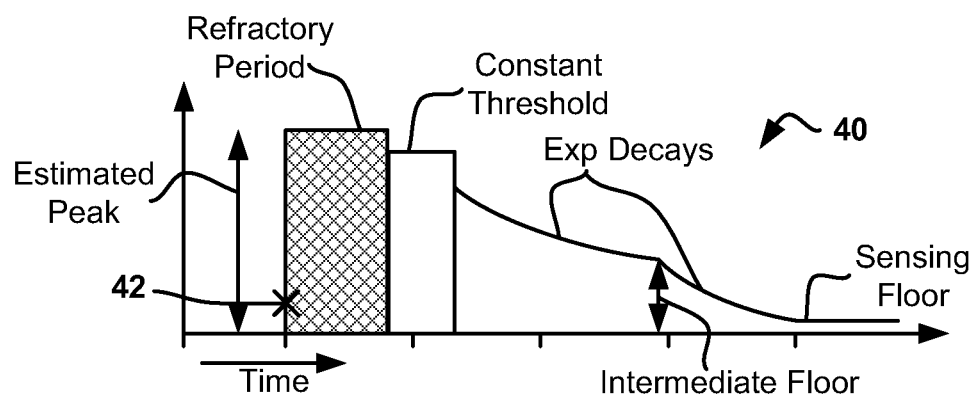

FIGS. 2-3 show illustrative detection profiles. In order to analyze an implantee's cardiac activity, an implanted medical device captures electrical signals using a combination of at least two implanted electrodes. A detection profile is an analytic tool used to identify cardiac events as perceived from the view of the implantable system. The detection profile is compared to the captured electrical signal(s) and, when the captured signal has a greater magnitude than that represented by the detection profile, a detected event is declared. Other detection profiles may be used. Other signal inputs, including physiological inputs captured using, for example, impedance detection, optical interrogation, chemical sensors, accelerometers, etc. may also be integrated in the system. Profiles may be used in association with single or multiple electrode vectors.

Additional examples and explanations of detection profiles may be found, for example, in U.S. Pat. No. 5,709,215 to Perttu et al. and/or commonly owned U.S. Provisional Patent Application No. 61/034,938, titled ACCURATE CARDIAC EVENT DETECTION IN AN IMPLANTABLE CARDIAC STIMULUS DEVICE, filed on Mar. 7, 2008, and U.S. patent application Ser. No. 12/399,901, now U.S. Pat. No. 8,565, 878, which claims benefit of and has the same title as the 61/034,938 Provisional Application. The illustrative detection profiles shown in FIGS. 2-3 vary in amplitude with time. This is typical but not required.

Referring now to FIG. 2, a detection profile 30 is shown relative to a most recent detected event is represented by the X at 32. Following the most recent detected event 32, the detection profile 30 enters a refractory period during which it does not identify additional cardiac events. The refractory period helps avoid repeatedly sensing the same cardiac cycle that led to the detected event at 32. A refractory period may last, for example, from tens to hundreds of milliseconds, depending upon the system design. Other refractory periods may be used.

Following the refractory period, the illustrative detection profile 30 undergoes decay to a sensing floor. The decay begins at an amplitude equal to, or a percentage of, the "estimated peak." The "estimated peak" is an estimate made by the implanted system of the electrical amplitude of cardiac events. For example, an estimated peak may be set to the peak amplitude sensed during the refractory period, a peak from a previous refractory period, or an average of peaks from a plurality of refractory periods. The estimated peak may be replaced with a fixed value. Some examples start exponential decay at 100% of the estimated peak; others use lesser fractions down to as low as 25%. The decay is shown as exponential; this is merely illustrative and other decay forms, such as stepped or constant slope may be used instead.

Another detection profile is shown in FIG. 3 at 40. Again, starting with a most recent detected event 42, the detection profile enters a refractory period. The refractory period is followed by a constant threshold period and two exponential decays, first to an intermediate floor and then to the sensing floor. Commonly owned U.S. Provisional Patent Application No. 61/034,938, titled ACCURATE CARDIAC EVENT DETECTION IN AN IMPLANTABLE CARDIAC STIMULUS DEVICE, filed on Mar. 7, 2008 (to which priority is claimed by regular applications including U.S. patent application Ser. Nos. 12/399,901 now U.S. Pat. No. 8,565,878, 12/399,914 now U.S. Pat. Nos. 8,160,686, and 12/437,547 now U.S. Pat. No. 8,160,687) discusses illustrative numerical examples of a detection profile as shown in FIG. 3.

The detection profile of FIG. 3 provides a number of additional variables that can be manipulated to achieve desired sensing/detection characteristics tailored to individual patients or predetermined conditions, including the amplitude of the constant threshold period, the amplitude of the intermediate floor, decay rate(s) or start and end points associated with the exponential decays, or durations associated with each of the refractory period, the constant threshold period, and the exponential decays. Durations, thresholds, and decay rates may be modified in response to inputs including detected rate, device state, detected noise, and/or similarity of estimated peaks for prior detected events.

For each of the examples shown in FIGS. 2-3, it should be appreciated that, for either detection profile 30, 40 a new detected event can be declared as soon as the refractory period ends. If a sufficiently large signal appears at the end of the refractory period, a new event will be declared. This helps to quickly identify fast cardiac rhythms. It also presents the opportunity for saturation of the input circuitry to cause erroneous high-rate calculations.

Saturation is a condition in which a circuit is driven to its maximum or minimum output and no longer responds to small changes in signal. Saturation may appear in the analog domain of a system and can be reflected in the digital domain of a system. For example, the input circuitry to a system can become saturated when a large amplitude signal is received and the input of the system reaches its dynamic range limits. Relative to cardiac event detection, if the system input circuitry becomes saturated, it is likely that a new detected event will be declared immediately following the end of refractory. As a result, during saturation, the duration of the refractory period may become the only limit to the rate at which events are detected. Saturation can cause calculation of very high event rates which an implanted device may characterize as tachyarrhythmia, triggering therapy. However, saturation is not itself an arrhythmic condition, so stimulus delivery in response to saturation is usually undesirable.

An external energy pulse can cause saturation of the inputs to an implantable system. One source of such a pulse may be an external defibrillator. For illustrative purposes, some of the following examples simulate what can occur when an external defibrillator is used on a patient who has an implanted cardiac stimulus or monitoring system. While an implanted device is usually configured to endure external defibrillation without sustaining damage, it is also desirable to provide the device with reliable sensing capabilities during or after such events. Input filtering circuitry of an implanted system may itself contribute to sensing difficulties, as the input circuitry may include passive filters using capacitors that can become charged and hold transient voltages following a saturation event; until the transient voltages on such passive components are discharged, sensing accuracy may suffer.

Thus, some embodiments operate in the following fashion: seek to identify saturation and, if saturation is identified, mitigate. Mitigation can take several forms including: modifying event detection; interrupting event detection; adjusting conversion of saturated analog signal into the digital domain; and accelerating recovery of the electrical system from saturation. Another example includes quantifying the effect of saturation and adding an equal, but opposite "signal" to the inputs to prevent overdetection. Illustrative examples are shown below.

Figure 4:
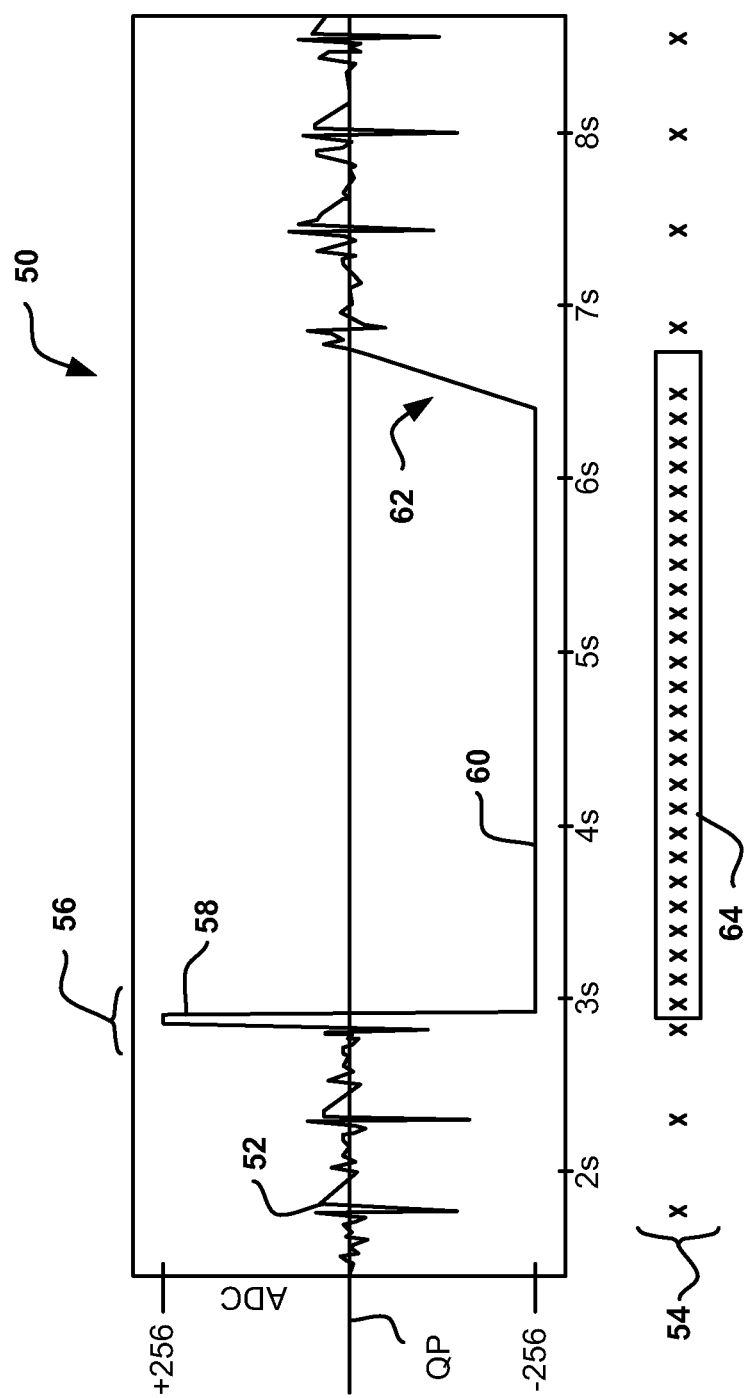
FIG. 4 shows a trace of a cardiac signal interrupted by saturation and markers associated with analysis of the signal.

FIG. 4 illustrates sensing behavior for an implantable system. An Analog-to-Digital converted (ADC) signal is represented at 50 along an axis centered around a quiescent point, with a range of −256 to +256 units ADC. The signal is shown as having what appears to be a cardiac signal with QRS complexes at 52. The amplitude of the signal at 52 is well within the ADC range. Detected events are indicated with an "x" beneath the graph, as shown at 54. At the time period shown at 56, an external stimulus is applied. In the example shown, stimulus is applied having a first portion shown as a large positive excursion 58 followed by a negative excursion that leaves the output of the system's ECG amplifier saturated at its negative limit, as shown at 60.

One reason for the relatively long negative excursion may be the use of analog filtering input circuitry having a combination of components with relatively long time constants, slowing recovery. If the implant's dynamic sensing range is in the range of a few millivolts and the stimulus is in the range of hundreds or even thousands of volts, the total amount of charge accumulated can prevent small signal operation of the input circuits. The charge on the input filtering circuitry of the system decays over time, but the system inputs remain saturated at the negative dynamic range limit as shown at 60. Eventually the system recovers, as shown at 62, ending saturation after a few seconds.

The long time period in saturation results in a number of fast detections, which are shown at 64. The fast detections 64 may be falsely counted as a high rate tachycardia or even ventricular fibrillation to the system, possibly resulting in a decision to deliver therapy. Some illustrative embodiments of the present invention apply rules to individual detection(s) to identify saturation and then apply mitigation strategy.

Figure 5:
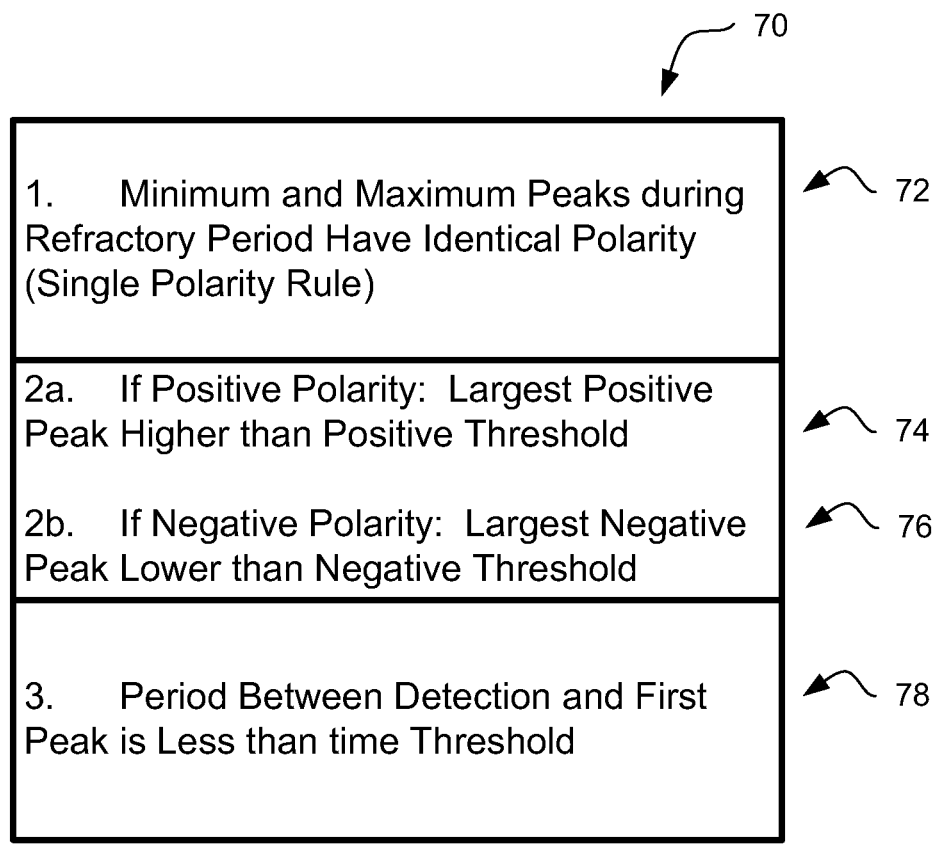
FIG. 5 shows a rule set for illustratively identifying a saturated detection.

FIG. 5 shows a set of rules that are applied in an illustrative embodiment to identify a saturated detected event. In this illustrative embodiment, these rules are used to analyze the signal captured following a detected event. The rules are shown at 70 and include the following: single polarity rule 72, large peak rules 74 and 76, and an early peak rule 78. In the illustrative example, if each of rules 72 and 78 are met and one of rules 74 and 76 is met, then saturation is identified. In other examples, reduced combinations of these rules may be used to identify saturation, without requiring all rules to be applied.

The single polarity rule 72 analyzes whether all samples of the captured signal during a given refractory period have the same polarity. For example, all samples may be positive, or all samples may be negative. If some samples are positive and others are negative, the rule 72 fails. In the illustrative example, this rule 72 is applied by observing whether the maximum and minimum peaks in the signal are of the same polarity.

The large peak rules 74 and 76 are separated into two rule statements to accommodate an unrectified signal analysis. The positive polarity rule is at 74, and determines whether the largest positive peak is above a predefined positive peak threshold, while a negative polarity rule is at 76 and determines whether the largest negative peak is lower (more negative) than a negative threshold. These rules 74, 76 indicate that the signal amplitude is large relative to available ADC output range. An illustrative example uses an ADC range of −256 to +256 units, and the respective limits for peak amplitude of these rules 74, 76 are set to +202 and −202 (+/−80%). Other limits may be used. The limit may change in response to other conditions such as rate. Rather than two rules, a single rule statement may simply refer to the absolute value of the amplitude, or a rule may be applied to rectified signals.

The early peak rule 78 checks whether the period between the detection and a "first peak" is less than a predetermined time threshold. In an example shown below, this rule is applied to a saturated signal by defining the peak as the first sample having no larger magnitude sample thereafter. In the example, if the entire refractory period is saturated such that all signals have the same ADC output value, then the very first sample would be marked as the "peak," since no larger sample follows. In an illustrative example, the early peak threshold is set to identify an early peak within the first two samples of the refractory period. The early peak rule 78 may be omitted, or it may be modified to allow the early peak to occur later in the signal.

An alternative approach to the single polarity rule 72 is a minimum amplitude rule. If the minimum amplitude is set to a large enough value, the system would not be able to change polarity without at least one sample falling below the minimum amplitude (due to slew rate limits). All signals passing this rule would be unipolar, though not all unipolar signals would be identified by this rule. Analyzing the rectified signal also allows a single statement of the amplitude rules 74, 76.

The rule set 70 provides an illustrative example of how a saturated detection may be identified. Other saturation identification rules may also be applied. The rules 72, 74, 76, 78 may be modified or replaced in other embodiments. For example, a minimum amplitude rule could be applied by itself, declaring saturation if every sample in the refractory period falls above (or below, for a negative polarity signal) a predetermined threshold. One such example would declare a saturated detection if all samples fall above 60% of the maximum dynamic range of the ADC output.

Figure 6:
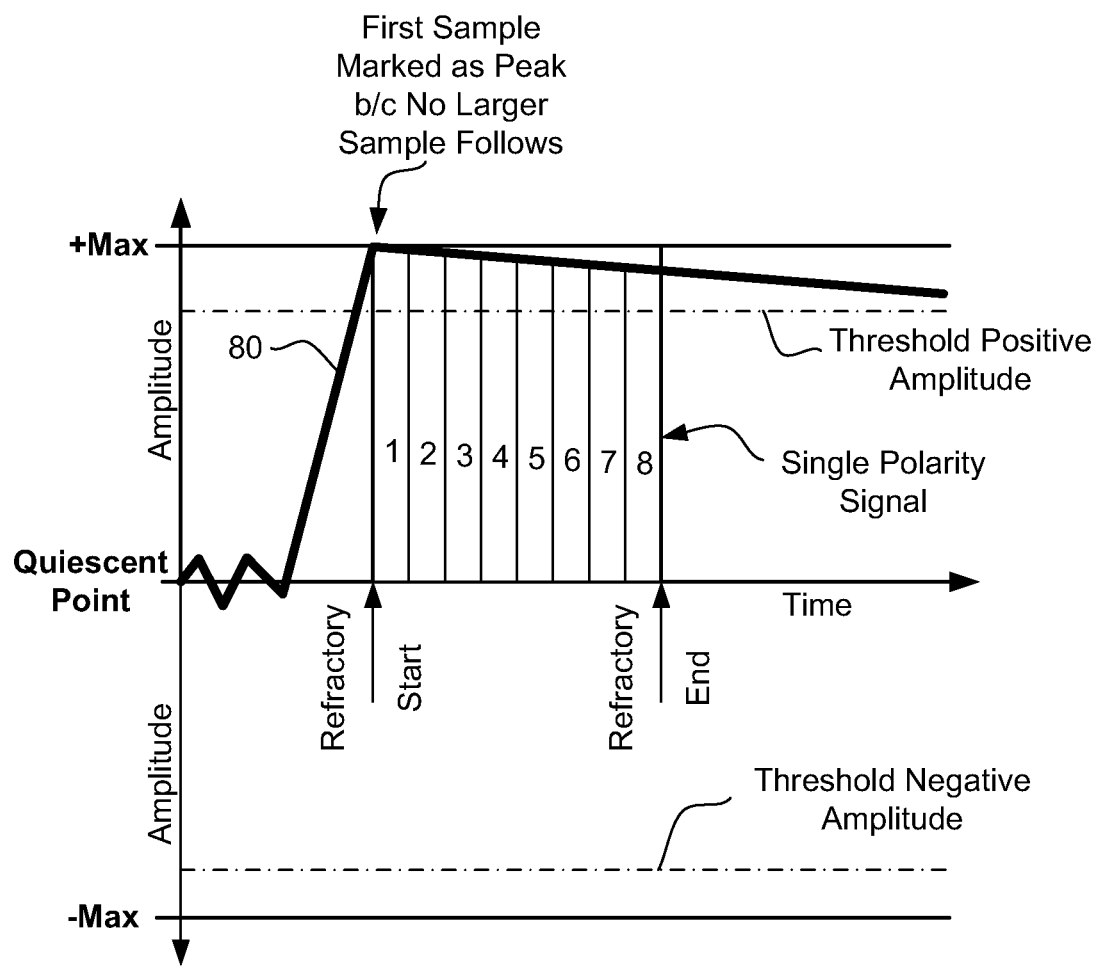
FIG. 6 shows applying the rules of FIG. 5 to a saturated detected event.

FIG. 6 shows application of the rule set 70 of FIG. 5 to an illustrative saturated signal. In FIG. 6, a signal trace is shown at 80, displayed against an ADC output scale having a range from −Max to +Max, with a quiescent point centered therebetween. During non-saturated operation, the signal trace 80 spends most of its time near the quiescent point, diverging away when a heart beat is detected, for example, as shown above in FIG. 4. During saturation, the trace 80 may not approach the quiescent point during a refractory period, for example as shown in FIG. 6.

A refractory period start and end are shown. For simplicity, eight samples are indicated by the blocks numbered [1-8] in the refractory period; most implementations would be designed with more samples during refractory. For example, one illustrative uses an approximately 156 ms refractory period such that 41 samples at 256 Hz are captured during refractory. Another example has 52 samples captured at 256 Hz, to yield an approximately 200 ms refractory period. Shorter and longer refractory periods, and higher or lower sampling rates may be used. In some examples, saturation rules may be applied using time periods that are not defined by refractory, for example, using a time period of 180 milliseconds without regard for the length of the refractory period. In yet another example, saturation may be identified using asynchronous analysis, in which any time period, regardless of detection, having predefined characteristics may trigger identification of saturation.

A detection occurs at the time of the Refractory Start, as shown. The very first sample [1] following the start of refractory is marked as a peak because no larger signal sample follows (meeting rule 72 of FIG. 5). The peak for the trace 80 is shown as exceeding the threshold positive amplitude for saturation (meeting rule 74 of FIG. 5). All of the samples [1-8] are shown as having positive polarity, relative to the quiescent point, making the signal 80 during the refractory period a single polarity signal (meeting rule 78 of FIG. 5). Since a rule set is satisfied, (rules 72, 74 and 78 of FIG. 5), the portion of the trace 80 in the refractory period is identified as saturated.

Trace 80 is not intended to simulate an actual signal. Saturation may appear as shown in FIG. 4, above, with the trace near or at one of the +Max or −Max lines across one or several consecutive refractory periods during saturation. The example shown indicates ongoing slow recovery from saturation by the downward slope of the trace 80.

Referring again to FIG. 5, in some embodiments, saturation is declared as soon as the rule set 70 is satisfied for a single detected event. In other embodiments, saturation may be declared after the rule set 70 is met for a number of consecutive detected events or, alternatively, if the rule set is met in a subset, A, out of a number of events, B, for example, in 4 out of 6 events. An A/B rule may be applied using larger or smaller sets of events. A secondary check where several detected events are considered may include observing whether the polarity of consecutive events is consistent.

In another example, if the received amplitude exceeds a saturation threshold, a counter is initiated and, if the counter reaches a predetermined value before the received amplitude drops below the saturation threshold, saturation is declared, without any reference to event detections. For example, supposing a 400 Hz sampling rate and 0 to 256 ADC count (rectified) analysis, a counter may begin counting up when a sample is received that exceeds a saturation threshold set to 75% of the maximum ADC output (in the example, 192 ADC counts). If the counter reaches 80 counts (200 milliseconds) and the sampled signal has not dropped below the threshold, saturation would be declared. Other sampling rates and ADC resolutions may be used, and operation in an unrectified signal may be performed.

In yet another example, if the maximum peak in the signal exceeds a saturation threshold and the slope characteristics of the signal meet defined rules, saturation may also be declared. In one example, a slope having no or a small number of turning points during a predefined time period can indicate saturation. For example, if there are less than 3 turning points in the signal during a predetermined period of time (such as 160 milliseconds), saturation may be declared. In yet another example, if there are less than 3 inflection points in the signal during a predetermined period of time, saturation may also be declared. Other thresholds for the number of inflection points and/or turning points may be used, and different durations may be considered. Turning point analysis may be part of a Waveform Appraisal analysis performed as in U.S. Pat. No. 7,248,921.

Once saturation is declared, one illustrative embodiment activates a Dynamic Heuristic Filter (DHF), the operation of which is explained by reference to FIGS. 7-9. Additional DHF embodiments are disclosed in commonly assigned U.S. patent application Ser. No. 11/497,204, now U.S. Pat. No. 7,623,913, titled IMPLANTABLE MEDICAL DEVICES USING HEURISTIC FILTERING IN CARDIAC EVENT DETECTION.

Figure 7:
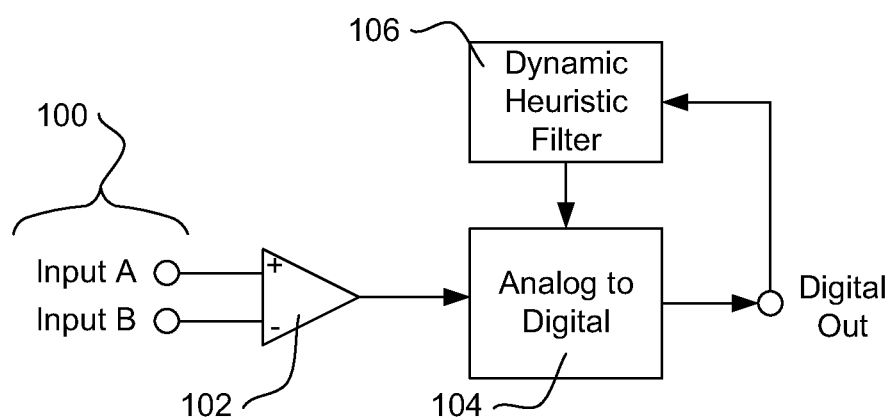
FIG. 7 is a high-level block schematic showing how an illustrative Dynamic Heuristic Filter may be applied to analog-to-digital conversion.

FIG. 7 provides a simple summary of the system using a DHF: Inputs A and B are coupled to implantable electrodes and fed into an ECG amplifier 102, the output of which is then converted to digital form by an ADC 104. This produces a digital output. The DHF 106 reads the digital output and modifies operation of the ADC 104 to move the average digital output toward a desired quiescent point. The "heuristic" part of the DHF is explained in FIG. 8, and the "dynamic" part of the DHF is explained below with reference to FIG. 9.

Figure 8:
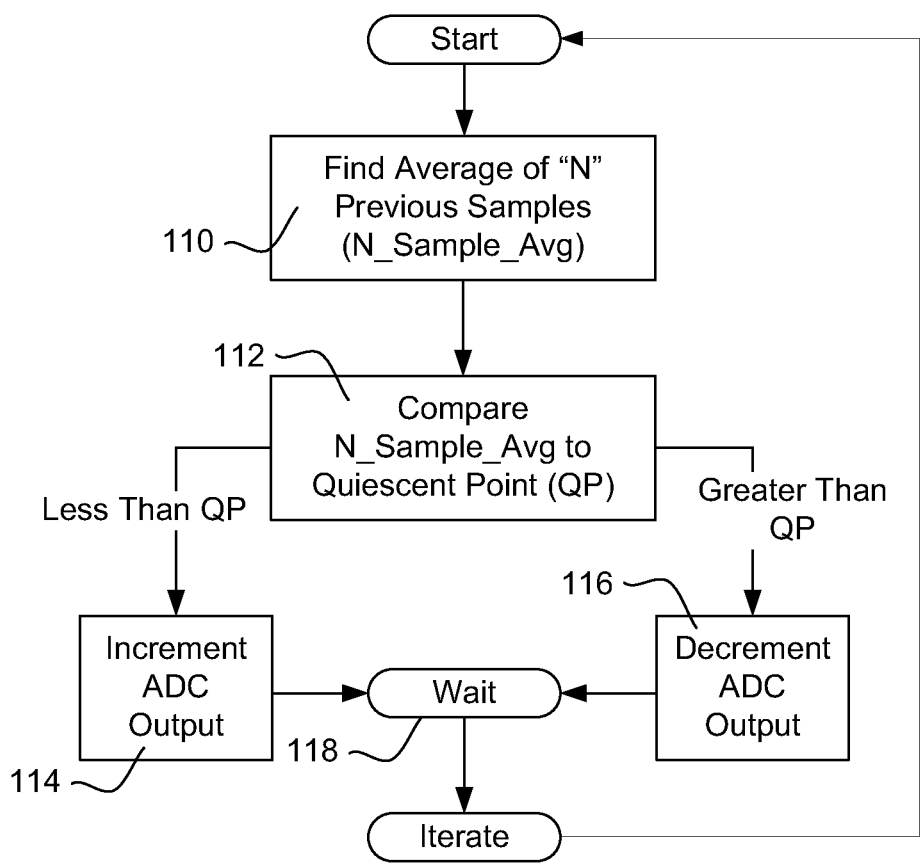
FIG. 8 is a block diagram illustrating a method of Heuristic Filtering.

Heuristic filtering can be performed as an iterative process as shown in FIG. 8. First, the average of a number "N" of previous ADC output samples is calculated, as shown at 110. For example, twenty-five ADC samples may be averaged. This yields a value, "N_Sample_Avg". Then, the N_Sample_Avg is compared to the desired quiescent point, as shown at 112. When the N_Sample_Avg is below the quiescent point, the ADC output is incremented (raised by one or more ADC counts), as shown at 114. When N_Sample_Avg is above the quiescent point, the ADC output is decremented (lowered by one or more ADC counts), as shown at 116. The method then awaits for a period of time to expire until a next iteration occurs as shown at 118.

In this fashion, Heuristic filtering moves the ADC output toward the quiescent point each time it is called. The Heuristic filtering can remove a DC offset from the ADC output, and thus operates as a form of high pass filter. In an illustrative example, Heuristic filtering is applied within a device using a default period of 63 milliseconds (16 iterations per second of the method in FIG. 8), using N=25 on a signal sampled at 256 Hz. Other default periods, N values, and sampling rates may be used in other embodiments. In the illustrative example, when the DHF operation is called, the system manipulates the period at which the Heuristic Filter is called as shown in FIG. 9.

Figure 9:
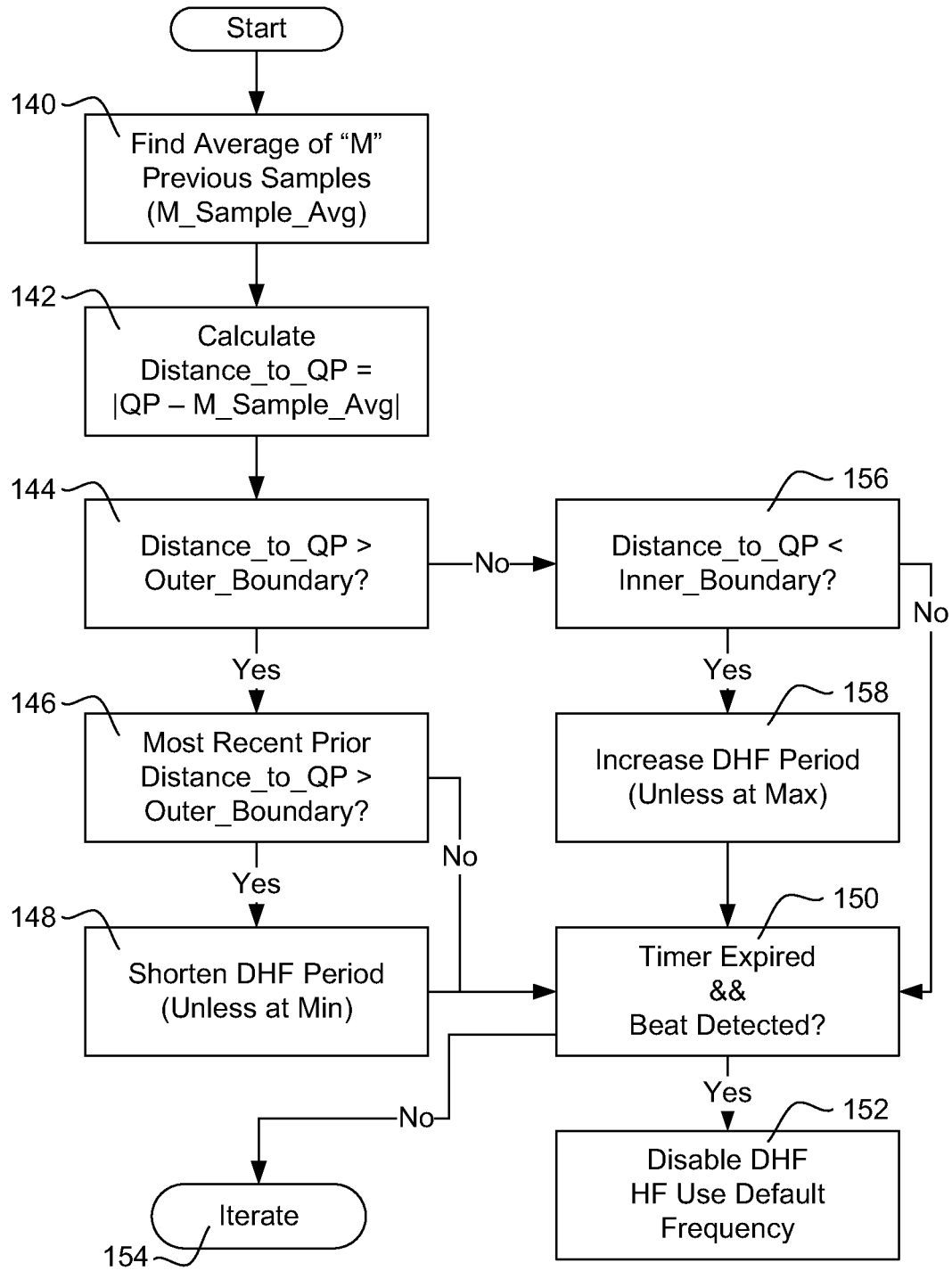
FIG. 9 is a block diagram illustrating control of a Dynamic Heuristic Filter period of operation.

FIG. 9 shows the "dynamic" aspect of the DHF. The DHF repeatedly performs the method of FIG. 8 at a DHF period of operation that becomes shorter when the signal is farther from the Quiescent Point, and longer when the signal is closer to the Quiescent point. When the DHF period of operation is shorter, the Heuristic filter is applied more often than when the DHF period of operation is longer. FIG. 9 shows how the DHF Period of operation is manipulated in an illustrative example. In addition to responding to saturation detection, the DHF may also be called following therapy output events, such as delivery of defibrillation or pacing stimulus, which may also cause transient saturation of the input circuitry of a system, or other potential offset-causing events such as changes to the sensing vector being used by the system, or delivery of stimulus for purposes of induction testing. Some examples appear in commonly assigned U.S. Pat. No. 7,623,913, titled IMPLANTABLE MEDICAL DEVICES USING HEURISTIC FILTERING IN CARDIAC EVENT DETECTION, the disclosure of which is incorporated herein by reference.

Once called, the function in FIG. 9 first finds the average of "M" previous samples to calculate "M_Sample_Avg" as shown at 140. In an illustrative example, M=6. Other values for M may be used. Next, the absolute value of the difference between M_Sample_Avg and the quiescent point is calculated and referred to as "Distance_to_QP" as shown at 142. Distance_to_QP is compared to a first threshold, Outer_Boundary, as shown at 144, to determine if the average sample value is well away from the quiescent point. If so, a recheck of the prior calculation of Distance_to_QP is performed, as shown at 146 (the recheck may be omitted, if desired). If the "Outer_Boundary" value is exceeded twice in a row, then the DHF Period is shortened, as shown at 148, unless it is already at a minimum period. This calls the function shown in FIG. 8 more often to reduce any DC offset coming out of the ADC quickly. Illustrative values for the DHF period of operation and outer boundary condition are provided below.

Once the DHF period of operation is recalculated in step 148, the method determines whether a timer has expired and a beat has been detected, as shown at 150. The timer ensures the DHF remains active for time sufficient to remove not only any saturation induced offset, but also to correct for any offset induced by recovery from saturation. In an illustrative example, the DHF timer expires after about 8 seconds of operation, regardless of the reason it is called. In another illustrative example, the DHF timer can be set to one of several values based on the reason it is called, for example, 8 seconds following delivery of a defibrillation therapy, and 4 seconds following identification of a likely saturated event. Once the DHF timer expires, the system continues to operate the DHF until a detected event occurs. The DHF timer may be omitted in other embodiments.

In another embodiment, after Saturation is declared, periodic Saturation Analysis periods may be defined (for example, a new Saturation Analysis period could start every 500 ms). Sampled data would then be analyzed to determine whether a set of saturation rules continues to be satisfied during the Saturation Analysis periods. In this instance, the DHF may be deactivated once the saturation rule set is no longer met. If desired, the different saturation rules may be applied during such saturation analysis periods than were applied to declare saturation. Alternatively, the same rules may be applied in both situations.

Once the timer expires, if a beat has been detected, the DHF is disabled and reverts to the default period of operation, as shown at 152. Thus, normal operation is resumed. In some embodiments, whether a beat is detected at 150 is determined using additional factors, for example, including waveform appraisal (such as shown in U.S. Pat. No. 7,248,921, or U.S. Provisional Patent Application No. 61/255,253) to ensure that a detection threshold crossing is not caused by noise, or using saturation rules to ensure the detected beat is not itself saturated. If the timer has not expired and/or no beat is detected at step 150, the method iterates as shown at 154. The order of steps may be modified in some embodiments, for example, the DHF disabling condition query at 150 may occur before step 140.

Going back through the diagram, if a No result occurs at step 144, the method determines whether Distance_to_QP is less than another variable, Inner_Boundary, as shown at 156. If so, then the DHF Period is extended, as shown at 158, unless it is already at the maximum period. This step 158 reduces the impact of the DHF on the ADC output as it nears the quiescent point. Following a No result at 156 or a DHF Period adjustment at 158, the method again reaches step 150.

In an illustrative example, the Outer_Boundary is applied at 80% of the Sensing Noise Floor (for example, with an ADC output of −256 to +256 and Sensing Noise Floor=5 ADC units, Outer_Boundary may be set to +/−4 ADC units). In another illustrative example, Inner_Boundary is set at 40% of the Sensing Noise Floor (for example, with an ADC output of −256 to +256 and Sensing Floor=5 ADC units, Inner_Boundary may be set to +/−2 ADC units). These examples may be used in combination with one another; other boundary values may be used instead. In an illustrative example, the default Heuristic filter period is about 63 milliseconds, with the maximum DHF filter period at that value as well, and the minimum DHF filter period is set to about 1 milliseconds, using factors of 2 therebetween. This yields possible DHF Periods, in the example, of about 1, 2, 4, 8, 16, 31 and 63 milliseconds. In an illustrative embodiment, the DHF method of FIG. 9 is called at intervals of 94 milliseconds in order to manipulate the DHF Period. Other DHF period values, DHF method call intervals, ADC resolution/ranges, sampling rates, and thresholds for Outer_Boundary and Inner_Boundary may be used as well, and these details are not intended to be limiting, but merely provide one relatively complete example.

Figure 10:
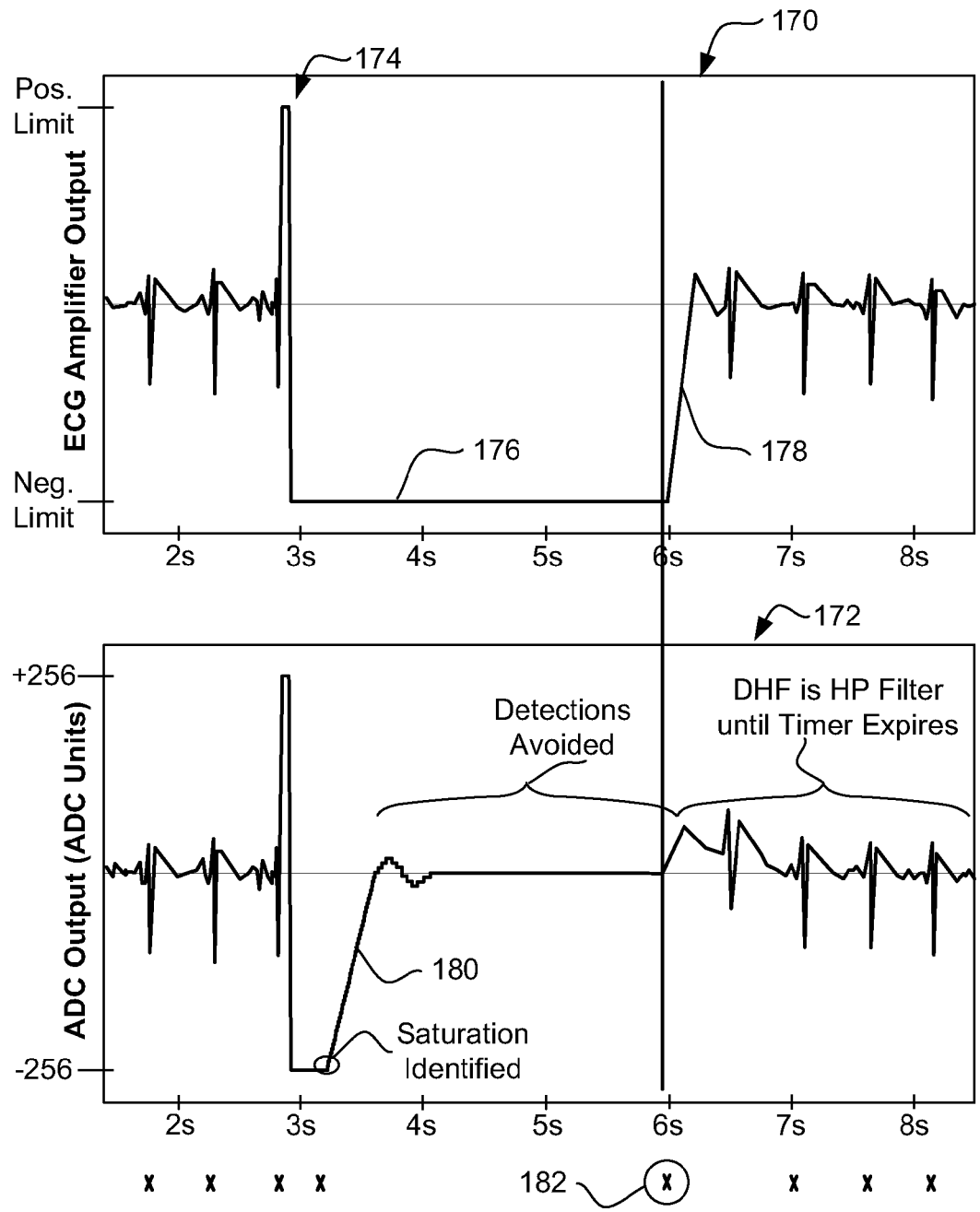
FIG. 10 compares ECG Amplifier Output and Digital Output for an illustrative example in which saturation is identified and mitigation is applied.

FIG. 10 compares the ECG Amplifier Output 170 to the ADC Output 172 during a saturation mitigation operation. Referring to the ECG Amplifier Output graphic 170, an external electrical impulse is again shown at 174. The external electrical impulse is shown with biphasic nature, resulting in the amplifier output going to its positive dynamic range limit and then to its negative dynamic range limit, where it remains as shown at 176. As the input circuitry recovers, small signal operation resumes, as shown at 178.

The ADC Output shown at 172, however, is impacted by the saturation mitigations put in place using methods as shown in FIGS. 5-9. In particular, when saturation starts, the rule set of FIG. 5 is used to identify a saturation event. Once saturation is identified, the DHF engages and drives the ADC output toward the quiescent point, as shown at 180.

When first engaged, the DHF may begin with its minimum period of operation enabled. The example shown uses a DHF implementation having Outer Boundary at +/−4 ADC, Inner Boundary at +/−2 ADC, minimum period of operation at 63 milliseconds, N=25, M=6, seven defined DHF periods of operation, adjusted at 94 mS intervals and operating on a signal sampled at 256 Hz, with a +/−256 bit ADC output resolution. Some implementations can cause ringing at the quiescent point, as shown. Those skilled in the art will recognize that ringing may be avoided by adjusting one or more of these values to produce a damped approach to the quiescent point, however, the quiescent point would then be approached less quickly.

The number of detections that occur during saturation is greatly reduced, as can be seen by comparing FIG. 10 to FIG. 4. As shown in FIG. 10, a detected event 182 occurs after the ECG Amplifier Output 170 nears the center of it dynamic range. By this point, cardiac signals are again captured and, following the saturation, normal detection resumes, with the DHF continuing to operate as a high-pass filter until its timer expires.

The invocation of DHF is one approach to mitigate saturation that avoids extra detections due to saturation, but does not prevent detections caused by cardiac activity, as a response to saturation. Other embodiments may use other mitigations once saturation is identified.

In another illustrative embodiment, a different mitigation approach allows events to be detected without necessarily calling for the DHF, but corrects for erroneous events by identifying saturated detections. The rule set of FIG. 5 may be used to identify non-cardiac events. In such an embodiment, each of the detections during saturation in FIG. 4 (detections 64) could be identified as saturated by applying the rule set of FIG. 5.

In some embodiments, saturated detections can be marked as suspect events. In the illustrative embodiment, suspect events would not be further used in analysis of cardiac activity, and erroneous stimulus delivery based on miscounting of events during saturation can be avoided. Treatment of suspect events can be similar to that explained in U.S. patent application Ser. No. 12/399,914. Examples may also use waveform appraisal as described in U.S. Pat. No. 7,248,921 and/or U.S. Provisional Patent Application No. 61/255,249, both of which are incorporated herein by reference. Another embodiment may identify saturation by combining amplitude information with slope information to identify large amplitude events having few or no turning points or inflection points.

Other embodiments use alternatives to DHF to avoid saturation-induced detections. In one illustrative example, when saturation is identified, an implantable system uses a blanking period to avoid detection during saturation. For example, a blanking period of 1-5 seconds may be activated. Alternatively, a refractory period of 1-5 seconds may be applied. In these two examples, a blanking period is one in which incoming signals are not observed by the system (for example, the input amplifier or ADC may be powered off), while a refractory period is one in which incoming signal is observed, but detection of R-waves is inhibited. These examples are in contrast to the situation in which a device invokes blanking or refractory following its own delivery of a defibrillation or pacing therapy. Instead, the implanted device can invoke blanking or refractory following analysis of a detection (or group of detections) indicating saturation. The duration of a blanking or refractory period may vary beyond the parameters noted above and/or may be selected in view of analog circuit saturation recovery times for a given device.

In yet another illustrative example, identification of saturation leads to an input recharge operation. An input recharge operation may be used to accelerate recovery from saturation, for example, by applying a refractory or blanking period during which a reference voltage is applied to both the inverting and noninverting inputs of the ECG Amplifier (and/or other nodes of the input circuitry) to reduce any built-up charge. Some illustrative examples are disclosed in commonly assigned U.S. Pat. No. 7,623,916, titled IMPLANTABLE CARDIAC STIMULUS DEVICES AND METHODS WITH INPUT RECHARGE CIRCUITRY.

Figure 11:
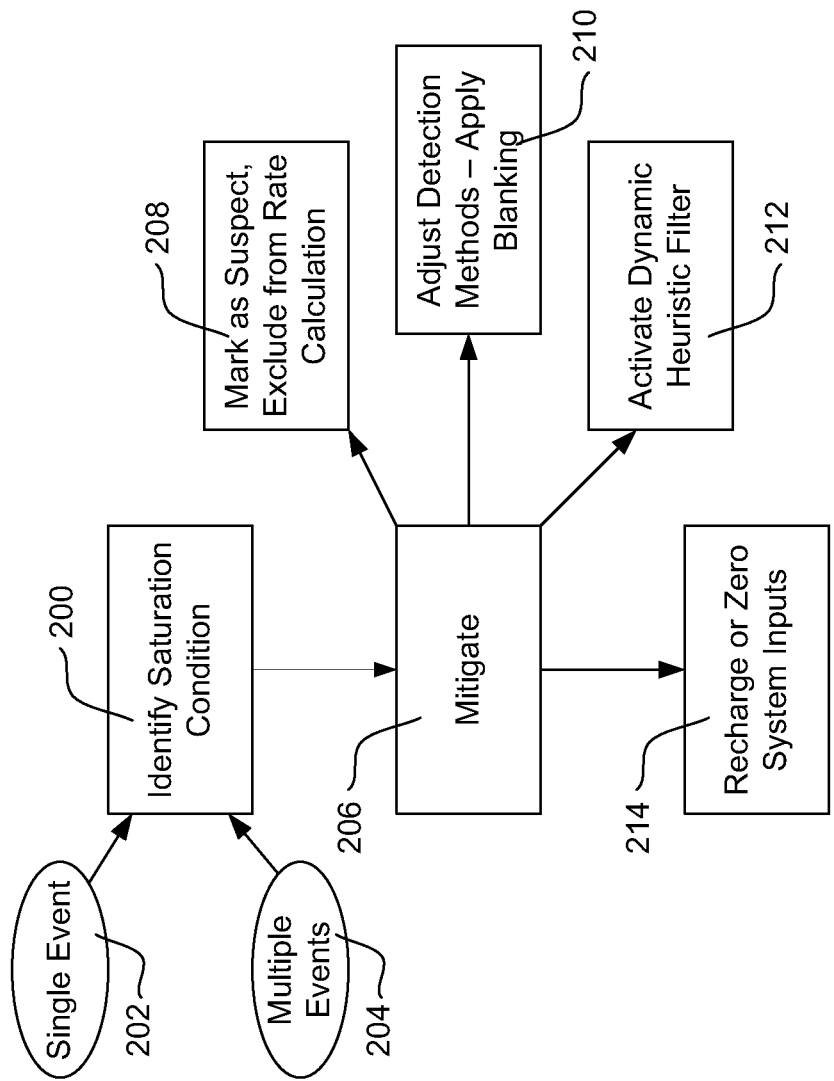
FIG. 11 is a high-level block diagram illustrating mitigations in response to identification of a saturated event.

FIG. 11 provides a further example. Saturation is identified as shown at 200 by reference to a single event 202 or multiple events 204. Following identification of saturation at 200, mitigation occurs as noted at 206. Mitigation can take several forms. As shown at 208, in some instances, individual detected events are analyzed to identify those caused by saturation, and saturation-induced events are excluded from further analysis such as rate analysis. As shown at 210, in some instances, detection methods may be adjusted, for example by the use of blanking or refractory periods. As shown at 212, in some instances, the analysis of captured signal is modified at the level of ADC to force the digitized signal to near its quiescent point during saturation by, for example, activating a Dynamic Heuristic Filter. Finally, in some instances as shown at 214, the effects of saturation can be mitigated by the use of input recharge circuitry to charge the system inputs to a desired range, or the input circuitry can be shorted out to zero system inputs, in an attempt to help the ECG amplifier into its small-signal operation more quickly than might otherwise occur. In addition to individual, separate use of these mitigations 208, 210, 212, 214, combinations of two, three or all of these approaches may be used.

As used herein, the term "saturated event" indicates an event that has been analyzed and found to have characteristics that indicate saturation. Such saturation may include saturation of input circuitry that is likely to impair a system's capability for accurate cardiac event detection. No further meaning is intended, and no specific circuit design or state is meant.

In some embodiments, saturation is identified by analysis of digital data received from analog components of an implantable cardiac stimulus/monitoring device. In one example, events are detected in the digital data and then analyzed to identify saturation (for example using rules as set forth above). A multi-tier response can be made. First, a response to saturation may take place at the sensing input circuitry, such as applying an electrical output to offset saturation or to zero out saturation for example by applying a reference voltage signal as methods discussed in U.S. Pat. No. 7,623,916, titled IMPLANTABLE CARDIAC STIMULUS DEVICES AND METHODS WITH INPUT RECHARGE CIRCUITRY. Second, the analog-to-digital conversion circuitry may be placed in a state that aggressively drives the digital signal toward its quiescent point, such as the dynamic Heuristic filtering discussed in U.S. Pat. No. 7,623,913, titled IMPLANTABLE MEDICAL DEVICES USING HEURISTIC FILTERING IN CARDIAC EVENT DETECTION. Third, data that is likely corrupted by saturation may be corrected by identifying saturated detected events (for example using rules as set forth above) and removing them from analysis. Not all tiers of response are necessary to various embodiments, and each may be used separately or in pairs as well.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable cardiac stimulus device (ICSD) comprising electrodes for capturing signals and operational circuitry configured for analyzing captured signals, wherein the operational circuitry is configured to identify saturation of input signals by the following method:

detecting an event in a captured signal, wherein the event is detected if captured signal amplitude exceeds a detection threshold;

analyzing the detected event for characteristics indicating saturation; and if the detected event has characteristics indicating saturation, identifying the detected event as saturated and engaging a mitigation in response to the saturation;

wherein the operational circuitry is configured such that, in the step of analyzing the detected event for characteristics indicating saturation, the following steps are performed:

across a defined period of time, signal samples are analyzed to identify a largest signal sample during the defined period of time and to determine whether:
i) the signal samples are all of a single polarity;
ii) the largest signal sample exceeds a saturation amplitude threshold; and
iii) the largest signal sample occurs within a predetermined number of samples of the start of the defined period of time;
and if each of i), ii) and iii) is true, the operational circuitry determines that the detected event has characteristics indicating saturation.

2. The ICSD of claim 1 wherein the operational circuitry is configured such that the mitigation comprises activation and operation of a dynamic Heuristic filter (DHF) operated by the operational circuitry as follows:

on activation, the DHF is initialized with an initial period of operation that defines how often a Heuristic filter is called;
when the Heuristic filter is called, a feature of analog-to-digital conversion (ADC) is adjusted to move an average ADC output toward a quiescent point;
at a defined DHF call interval, the DHF period of operation is recalculated by analyzing the distance of a typical ADC output from the quiescent point;
wherein the average ADC output is calculated using an average of a selected number, N, of ADC outputs, and the typical ADC output is calculated using an average of a selected number, M, of ADC outputs.

3. The ICSD of claim 2 wherein the operational circuitry is configured such that the step of periodically recalculating the DHF period of operation either:

decreases the DHF period of operation when the typical ADC output is relatively farther from the quiescent point; or
increases the DHF period of operation when the typical ADC output is relatively closer to the quiescent point.

4. The ICSD of claim 1 wherein the operational circuitry is configured such that the mitigation response comprises excluding a detected event that has characteristics indicating saturation from further analysis, including rate calculation and rhythm analysis.

5. An implantable cardiac stimulus device (ICSD) comprising electrodes for capturing signals and operational circuitry configured for analyzing captured signals, wherein the operational circuitry is configured to identify saturation of input signals by the following method:

detecting an event in a captured signal, wherein the event is detected if captured signal amplitude exceeds a detection threshold;
analyzing the detected event for characteristics indicating saturation; and
if the detected event has characteristics indicating saturation, identifying the detected event as saturated and engaging a mitigation in response to the saturation;
wherein the operational circuitry is configured such that, in the step of analyzing the detected event for characteristics indicating saturation, the following characteristics are analyzed:
whether the detected event is associated with a signal amplitude that crosses a saturation amplitude threshold; and
if so, whether less than a saturation threshold number of signal turning points occur during a predetermined period of time associated with the detected event.

6. An implantable cardiac stimulus device (ICSD) comprising electrodes for capturing signals and operational circuitry configured for analyzing captured signals, wherein the operational circuitry is configured to identify saturation of input signals by the following method:

detecting an event in a captured signal, wherein the event is detected if captured signal amplitude exceeds a detection threshold;
analyzing the detected event for characteristics indicating saturation; and
if the detected event has characteristics indicating saturation, identifying the detected event as saturated and engaging a mitigation in response to the saturation;
wherein the operational circuitry is configured such that, in the step of analyzing the detected event for characteristics indicating saturation, the following characteristics are analyzed:
whether the detected event is associated with a signal amplitude that crosses a saturation amplitude threshold; and
if so, whether less than a saturation threshold number of signal inflection points occur during a predetermined period of time associated with the detected event.

7. An implantable cardiac stimulus device (ICSD) comprising electrodes for capturing signals and operational circuitry configured for analyzing captured signals, wherein the operational circuitry is configured to identify saturation of input signals by the following method:

detecting an event in a captured signal, wherein the event is detected if captured signal amplitude exceeds a detection threshold;
analyzing the detected event for characteristics indicating saturation; and
if the detected event has characteristics indicating saturation, identifying the detected event as saturated and engaging a mitigation in response to the saturation;
wherein the operational circuitry is configured such that the mitigation response comprises applying a signal to the inputs to the system to reduce saturation energy at the inputs.

8. An implantable cardiac stimulus device (ICSD) comprising electrodes for capturing signals and operational circuitry configured for analyzing captured signals, wherein the operational circuitry is configured to identify saturation of input signals by the following method:

detecting an event in a captured signal, wherein the event is detected if captured signal amplitude exceeds a threshold;
analyzing the detected event for characteristics indicating saturation; and
if the detected event has characteristics indicating saturation, identifying the detected event as saturated and engaging a mitigation in response to the saturation;
wherein the mitigation comprises activation and operation of a dynamic Heuristic filter (DHF) operated by the operational circuitry as follows:
on activation, the DHF is initialized with an initial period of operation that defines how often a Heuristic filter is called;
when the Heuristic filter is called, a feature of analog-to-digital conversion (ADC) is adjusted to move an average ADC output toward a quiescent point;

the DHF period of operation is periodically recalculated in view of the distance of a typical ADC output from the quiescent point;

the average ADC output is calculated using an average of a selected number, N, of ADC outputs, and the typical ADC output is calculated using an average of a selected number, M, of ADC outputs; and the step of periodically recalculating the DHF period of operation either: decreases the DHF period of operation when the typical ADC output is relatively farther from the quiescent point; or increases the DHF period of operation when the typical ADC output is relatively closer to the quiescent point; and wherein in the step of analyzing the detected event for characteristics indicating saturation, signal samples within a predetermined time interval are analyzed to identify a largest signal sample and to determine whether:
i) the signal samples are all of a single polarity;
ii) the largest signal sample exceeds a saturation amplitude threshold; and
iii) the largest signal sample occurs within a predetermined number of samples of the start of the defined period of time;

and if each of i), ii) and iii) is true, the operational circuitry determines that the detected event has characteristics indicating saturation.

9. A method of operation in an implantable cardiac stimulus device (ICSD) comprising electrodes for capturing signals and operational circuitry configured for analyzing captured signals, the method comprising:

detecting an event in a signal captured using the electrodes, wherein the event is detected if captured signal amplitude exceeds a threshold;

analyzing the detected event for characteristics indicating saturation; and if the detected event has characteristics indicating saturation, identifying the detected event as saturated and engaging a mitigation in response to the saturation;

wherein, in the step of analyzing the detected event for characteristics indicating saturation, it is determined whether, across a defined period of time, rectified signal samples all have amplitudes that are in excess of a saturation threshold and, if so, the operational circuitry determines that the detected event has characteristics indicating saturation; and wherein the mitigation comprises activation and operation of a dynamic Heuristic filter (DHF) operated by the operational circuitry as follows:

on activation, the DHF is initialized with an initial period of operation that defines how often a Heuristic filter is called;

when the Heuristic filter is called, a feature of analog-to-digital conversion (ADC) is adjusted to move an average ADC output toward a quiescent point; and periodically recalculating the DHF period of operation in view of the distance of a typical ADC output from the quiescent point;

wherein the average ADC output is calculated using an average of a selected number, N, of ADC outputs, and the typical ADC output is calculated using an average of a selected number, M, of ADC outputs.

10. The method of claim 9 wherein the step of periodically recalculating the DHF period of operation either:

decreases the DHF period of operation when the typical ADC output is relatively farther from the quiescent point; or increases the DHF period of operation when the typical ADC output is relatively closer to the quiescent point.

11. The method of claim 9 wherein the mitigation response comprises applying a signal to the inputs to the system to reduce saturation energy at the inputs.

12. A method of operation in an implantable cardiac stimulus device (ICSD) comprising electrodes for capturing signals and operational circuitry configured for analyzing captured signals, the method comprising:

detecting an event in a signal captured using the electrodes, wherein the event is detected if captured signal amplitude exceeds a threshold;

analyzing the detected event for characteristics indicating saturation; and if the detected event has characteristics indicating saturation, identifying the detected event as saturated and engaging a mitigation in response to the saturation;

wherein, in the step of analyzing the detected event for characteristics indicating saturation, the following steps are performed:

across a defined period of time, signal samples that are analyzed to identify a largest signal sample during the defined period of time and to determine whether:
i) the signal samples are all of a single polarity;
ii) the largest signal sample exceeds a saturation amplitude threshold; and
iii) the largest signal sample occurs within a predetermined number of samples of the start of the defined period of time;

and if each of i), ii) and iii) is true, the operational circuitry determines that the detected event has characteristics indicating saturation.

13. A method of operation in an implantable cardiac stimulus device (ICSD) comprising electrodes for capturing signals and operational circuitry configured for analyzing captured signals, the method comprising:

detecting an event in a signal captured using the electrodes, wherein the event is detected if captured signal amplitude exceeds a threshold;

analyzing the detected event for characteristics indicating saturation; and if the detected event has characteristics indicating saturation, identifying the detected event as saturated and engaging a mitigation in response to the saturation;

wherein, in the step of analyzing the detected event for characteristics indicating saturation, the following characteristics are analyzed:

whether the detected event is associated with a signal amplitude that crosses a saturation amplitude threshold; and if so, whether less than a saturation threshold number of signal turning points occur during a predetermined period of time associated with the detected event.

14. A method of operation in an implantable cardiac stimulus device (ICSD) comprising electrodes for capturing signals and operational circuitry configured for analyzing captured signals, the method comprising:

detecting an event in a signal captured using the electrodes, wherein the event is detected if captured signal amplitude exceeds a threshold;

analyzing the detected event for characteristics indicating saturation; and if the detected event has characteristics indicating saturation, identifying the detected event as saturated and engaging a mitigation in response to the saturation;

wherein, in the step of analyzing the detected event for characteristics indicating saturation, the following characteristics are analyzed:
whether the detected event is associated with a signal amplitude that crosses a saturation amplitude threshold; and
if so, whether less than a saturation threshold number of signal inflection points occur during a predetermined period of time associated with the detected event.

15. A method of operation in an implantable cardiac stimulus device (ICSD) comprising electrodes for capturing signals and operational circuitry configured for analyzing captured signals, the method comprising:
detecting an event in a signal captured using the electrodes, wherein the event is detected if captured signal amplitude exceeds a threshold;
analyzing the detected event for characteristics indicating saturation; and
if the detected event has characteristics indicating saturation, identifying the detected event as saturated and engaging a mitigation in response to the saturation;
wherein, in the step of analyzing the detected event for characteristics indicating saturation, it is determined whether, across a defined period of time, rectified signal samples all have amplitudes that are in excess of a saturation threshold and, if so, the operational circuitry determines that the detected event has characteristics indicating saturation;
wherein the mitigation response comprises excluding a detected event that has characteristics indicating saturation from further analysis, including rate calculation.

16. A method of operation in an implantable cardiac stimulus device (ICSD) comprising electrodes for capturing signals and operational circuitry configured for analyzing captured signals, the method comprising:
detecting an event in a signal captured using the electrodes, wherein the event is detected if captured signal amplitude exceeds a threshold;
analyzing the detected event for characteristics indicating saturation; and
if the detected event has characteristics indicating saturation, identifying the detected event as saturated and engaging a mitigation in response to the saturation;
wherein:
the mitigation comprises activation and operation of a dynamic Heuristic filter (DHF) operated by the operational circuitry as follows:
on activation, the DHF is initialized with an initial period of operation that defines how often a Heuristic filter is called;
when the Heuristic filter is called, a feature of analog-to-digital conversion (ADC) is adjusted to move an average ADC output toward a quiescent point;
the DHF period of operation is periodically recalculated in view of the distance of a typical ADC output from the quiescent point;
the average ADC output is calculated using an average of a selected number, N, of ADC outputs, and the typical ADC output is calculated using an average of a selected number, M, of ADC outputs; and
the step of periodically recalculating the DHF period of operation either: decreases the DHF period of operation when the typical ADC output is relatively farther from the quiescent point; or increases the DHF period of operation when the typical ADC output is relatively closer to the quiescent point;
in the step of analyzing the detected event for characteristics indicating saturation, the following steps are performed:
across a defined period of time, signal samples are analyzed to identify a largest signal sample during the defined period of time and to determine whether:
i) the signal samples are all of a single polarity;
ii) the largest signal sample exceeds a saturation amplitude threshold; and
iii) the largest signal sample occurs within a predetermined number of samples of the start of the defined period of time; and
if each of i), ii) and iii) is true, the operational circuitry determines that the detected event has characteristics indicating saturation.

17. A method of cardiac event detection in an implantable cardiac stimulus system, the implantable cardiac stimulus system including operational circuitry configured for implantation in a patient and electrodes coupled to the operational circuitry, the method comprising:
the operational circuitry capturing a signal from the electrodes coupled thereto;
the operational circuitry analyzing the captured signal to detect a potential cardiac event;
the operational circuitry analyzing the detected potential cardiac event to determine whether the captured signal is likely saturated;
if the captured signal is likely saturated, the operational circuitry ignoring the detected potential cardiac event; and
if the captured signal is likely saturated, the operational circuitry responding to the likely saturated event by providing a signal to the input circuitry of the implantable cardiac stimulus system to offset the saturation.

18. The method of claim 17 wherein the step of analyzing the captured signal includes the operational circuitry performing analog-to-digital conversion of the captured signal and the method further comprises, if the captured signal is likely saturated, the operational circuitry adjusting the analog-to-digital conversion to drive output of the analog-to-digital conversion toward a predetermined quiescent point.

* * * * *